United States Patent [19]
Dye

[11] Patent Number: 5,935,174
[45] Date of Patent: Aug. 10, 1999

[54] ACETABULAR SHELL HAVING FLEXIBLE DOME HOLE DIAPHRAGM

[75] Inventor: Donald Dye, Pflugerville, Tex.

[73] Assignee: Sulzer Orthopedics Inc., Austin, Tex.

[21] Appl. No.: 08/970,926

[22] Filed: Nov. 14, 1997

[51] Int. Cl.⁶ .................................................. A61F 2/32
[52] U.S. Cl. ................................................... 623/22
[58] Field of Search ......................... 623/16, 18, 20, 623/22, 23

[56] References Cited

U.S. PATENT DOCUMENTS

| | | | |
|---|---|---|---|
| 4,077,070 | 3/1978 | Sivash | 623/22 |
| 4,666,450 | 5/1987 | Kenna | 623/22 |
| 4,963,154 | 10/1990 | Anapliotis et al. | 623/22 |
| 5,549,694 | 8/1996 | Noiles et al. | 623/22 |
| 5,609,648 | 3/1997 | Oehy et al. | 623/22 |
| 5,645,606 | 7/1997 | Oehy et al. | 623/22 |
| 5,782,929 | 7/1998 | Sederholm | 623/22 |

*Primary Examiner*—David J. Isabella
*Attorney, Agent, or Firm*—Philip S. Lyren

[57] ABSTRACT

An acetabular shell has a dome hole at the apex that is occluded at the proximal end thereof by a flexible diaphragm affixed to the shell wall of the acetabular shell. The flexible diaphragm moves between a first position spaced from an open proximal end of the dome hole to a second position engaging the open proximal end of the dome hole. Movement of the diaphragm is effected by seating the acetabular shell against the prepared bone of the acetabulum. The position of the diaphragm can be discerned through an open distal end of the dome hole either visually, or tacitly using a suitable feeler probe. The dome hole remains occluded against passage of debris therethrough regardless of the position of the flexible diaphragm.

27 Claims, 4 Drawing Sheets

ACETABULAR SHELL HAVING FLEXIBLE DOME HOLE DIAPHRAGM

BACKGROUND OF THE INVENTION

1. Field of the Invention

The present invention relates generally to implantable prostheses for replacing human skeletal joints, and relates more particularly to an acetabular cup component of a total hip prosthesis.

2. Background Information

An implantable total hip prosthesis includes a femoral component and an acetabular cup component. The femoral component, typically made of a bio-compatible metal such as titanium, titanium alloy or cobalt chrome alloy, has a distal stem and a proximal spherical head. As used herein, the words proximal and distal are terms of reference that indicate a particular portion of a prosthesis component according to the relative disposition of the portion when the component is implanted. "Proximal" indicates that portion of a component nearest to the torso, whereas "distal" indicates that portion of the component farthest from the torso. The distal stem is configured to be received and fixed within the medullary canal of a femur. The femur is prepared to receive the distal stem by resecting the natural head and neck, and reaming the exposed proximal medullary canal. The proximal end of the femoral component has a neck and attached spherical head that, supported by the distal stem anchored in the medullary canal, extend from the resected proximal end of the femur to replace the natural neck and head of the proximal femur. The proximal spherical head may be integral with the neck and stem of the femoral component, or may be removably attachable to the neck by way of a locking taper connection, sometimes known as a Morse taper. The acetabular cup component is configured to be received and fixed within the acetabulum of a pelvis. The pelvis is prepared to receive the acetabular cup by reaming a concavity in the acetabular bone. The acetabular cup component typically has an outer surface conforming to the concavity reamed in the acetabular bone of the pelvis, and an inner bearing cavity for receiving the head of the femoral component. The head articulates in the bearing cavity as a ball and socket to restore motion to a diseased or damaged hip joint.

One known type of acetabular cup involves an acetabular shell made of a bio-compatible metal such as titanium or a titanium alloy, and a bearing insert made of a bio-compatible polymer such as ultra-high molecular weight polyethylene. The acetabular shell is shaped generally as a hemispherical cup having a dome, or apex, at a proximal end and an annular rim at a distal end. Between the dome and rim, the acetabular shell comprises a shell wall defined by a generally convex proximal surface and a generally concave distal surface spaced from the proximal surface. The concave distal surface defines a shell cavity having an opening at the rim of the cup for receiving the bearing insert. The bearing insert has a generally convex proximal surface configured to be received and fixed within the acetabular shell in generally congruent engagement with the concave distal surface of the shell wall. The bearing insert also has a bearing cavity that opens distally for receiving the head of the femoral component. The bearing cavity is defined by a generally spherical concave bearing surface having a radius similar to that of the femoral head component. The concave bearing surface articulates against the surface of the spherical femoral head component.

Acetabular shells of the type described can be affixed to the acetabular bone by bone screws or bone cement. If bone screws are elected, the screws are driven into the bone through the screw holes before the bearing insert is placed into the shell. The shell also can be affixed by a combination of bone screws and bone cement. The acetabular shell can be provided with more screw holes than typically would be used by the implanting physician. This provides a selection of sites for placement of the bone screws, as may be dictated by the condition of the patient's pelvic bone or by the physician's preference. Some of the provided screw holes may receive a screw while others do not. For reasons explained below, it is desirable to provide means for occluding those screw holes that will not receive a screw.

Commonly, acetabular shells of the type described also include a dome hole at the apex. A typical dome hole is coaxially aligned with the axis of symmetry of the acetabular shell and extends through the shell wall from the concave distal surface to the convex proximal surface of the acetabular shell. Often, the dome hole is internally threaded or otherwise configured for receiving an instrument for holding and positioning the acetabular shell during implantation. Also, many physicians use the dome hole to obtain visual or tactile access to the reamed acetabular bone during implantation of the acetabular shell. Such access allows the physician to confirm that the acetabular shell is fully seated in engagement with the reamed bony surface of the acetabulum. By looking through the dome hole from the distal side of the shell, or by probing through the dome hole from the distal side of the shell with an elongate, bent, pointed instrument, the physician can discern whether space exists between the proximal opening of the dome hole and the adjacent acetabular bone. If such space exists, then the acetabular shell is not fully seated and the physician must make appropriate corrections to fully seat the acetabular shell in close engagement with the bone. As with the screw holes, for reasons explained below, it is also desirable to provide means for occluding the dome hole.

The bearing insert is usually designed to be received within the acetabular shell in nonarticulating relative relationship. Nevertheless, a small amount of unintended relative motion is believed to occur between the bearing insert and the acetabular shell in response to the varying load borne by the acetabular cup during use. Such small relative motion, or micro-motion, may result in wear at the interface between the bearing insert and acetabular shell that generates fine polyethylene or metal debris. According to some hypotheses, such debris can migrate out of the acetabular cup and contact bone, possibly resulting in osteolysis, which ultimately can lead to bone resorption and possible loosening of the acetabular prosthesis. One apparent pathway for the migration of debris out of the acetabular shell is through open screw holes. Another apparent pathway is through an open dome hole.

Various proposals for selectively occluding screw holes and dome holes in prosthetic acetabular shells are known in the art. The present invention is particularly directed to providing a means for occluding a dome hole while preserving the shell positioning and seating confirmation functions of the dome hole. It would be desirable to provide an acetabular shell, designed for use with a bearing insert, having a dome hole that can receive a holding and positioning instrument and that allows the physician to confirm that the acetabular shell has been fully seated against bone. The present invention provides these and other desirable advantages.

SUMMARY OF THE INVENTION

An acetabular shell is provided having a dome hole. In the shell as delivered to the surgeon, the dome hole is occluded to prevent migration of wear debris therethrough. Nevertheless, the dome hole can receive a shell-positioning instrument and can allow visual and tactile confirmation that the shell is fully seated against bone, without removing the occlusion.

According to one aspect of the present invention, an acetabular component for an implantable hip joint prosthesis includes a generally cup-shaped acetabular shell having a convex proximal surface and a concave distal surface defining a shell wall therebetween. The shell wall has an apex and an annular rim, and has a dome hole therethrough at the apex. The dome hole has an open proximal end and an open distal end. A flexible diaphragm is affixed to the shell and occludes the open proximal end of the dome hole. The flexible diaphragm is flexibly moveable between a first position and a second position. In the first position, the flexible diaphragm is spaced from the open proximal end of the dome hole. In the second position, the flexible diaphragm engages the open proximal end of the dome hole.

The flexible diaphragm moves from its first to its second position as the acetabular component is seated against the prepared bone of the acetabulum, thereby closing the space between the flexible diaphragm and the open proximal end of the dome hole. The movement can be discerned through the open distal end of the dome hole either visually, or tacitly using a suitable feeler probe.

It is an object of the present invention to provide an acetabular shell having a dome hole, occluded to prevent migration of wear debris therethrough, which can receive a shell-positioning instrument and allow visual and tactile confirmation that the shell is fully seated against bone.

Other objects and advantages of the present invention will be apparent from the following descriptions of the preferred embodiment illustrated in the drawings.

DESCRIPTION OF THE PREFERRED EMBODIMENT

Figure 1:
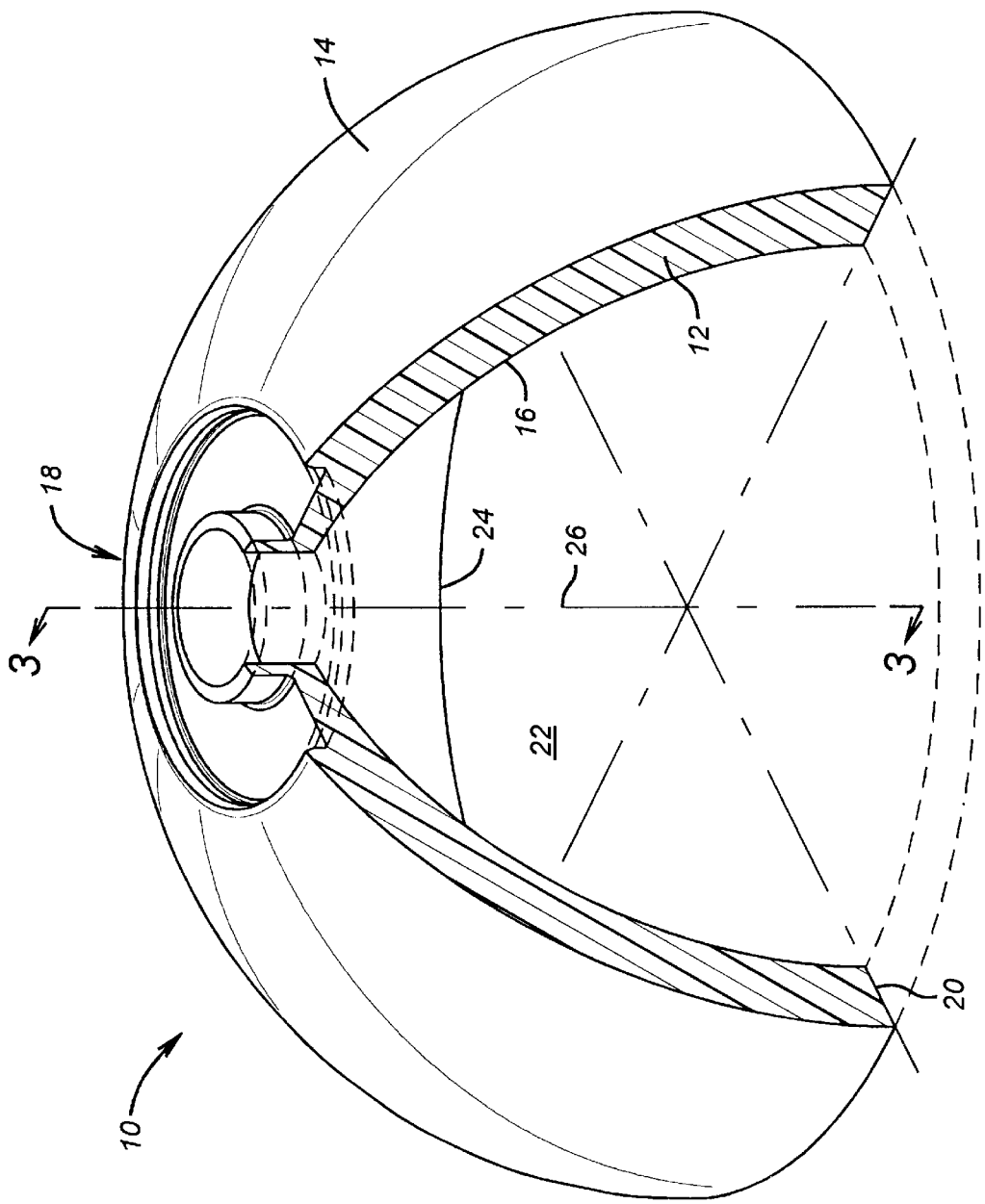
FIG. 1 is a perspective view, partially cut away, showing an acetabular shell constructed in accordance with the present invention.

Referring to the drawings, FIGS. 1–5, a preferred embodiment of the present invention is illustrated in the form of an implantable orthopedic prosthesis, particularly an acetabular shell component of a total hip joint prosthesis. The illustrated acetabular shell is useful as one component of that well-known type of total hip joint prosthesis that includes an acetabular shell and an associated bearing liner, and a femoral stem and an associated spherical head. The spherical head, fixed to the femoral stem, articulates in a ball-and-socket arrangement within the bearing liner, with the bearing liner being essentially fixed within the acetabular shell. The femoral stem and acetabular shell are fixed to bone of the proximal femur and pelvic acetabulum, respectively. Only the acetabular shell is described in detail herein, as the various types and configurations of bearing liners and the means for affixing such bearing liners within an acetabular shell are well understood in the art. The illustrated acetabular shell is particularly advantageous for preventing potentially osteolytic polyethylene particles from migrating out of the acetabular shell, when used with a bearing liner made of ultra-high molecular weight polyethylene. The utility of the invention is not limited to the use of any particular bearing liner material, however.

Referring to FIG. 1, an acetabular shell 10 is shaped generally as a hemispherical cup having a shell wall 12 defined by a convex proximal surface 14 and a concave distal surface 16. Acetabular shell 10 has a proximal dome region 18 at the apex of shell wall 12 and an annular rim 20 at the distal end of shell wall 12. Concave distal surface 16 of shell wall 12 defines a shell cavity 22 having an opening 24 into and through which a bearing insert (not shown) can be received. The preferred bearing insert is made of ultra high molecular weight polyethylene and has a partially spherical bearing cavity that opens distally for receiving a spherical head of a femoral component (not shown) in a ball-and-socket articulating relationship. A means for affixing the bearing insert against axial and rotational displacement within shell cavity 22 is preferred. Such means, being numerous and well known in the art, are not described herein. Shell wall 12 is generally symmetrical about an axis 26 that passes through the center of proximal dome region 18 at the apex of shell wall 12. Convex proximal surface 14 can be provided with a macro-texture, micro-texture, porous coating or other surface feature that mechanically engages bone, that promotes or accepts ingrowth or ongrowth of bone, or that enhances adhesion of bone cement. Such surface features are well known in the art and the present invention can be used with or without such features.

Figure 3:
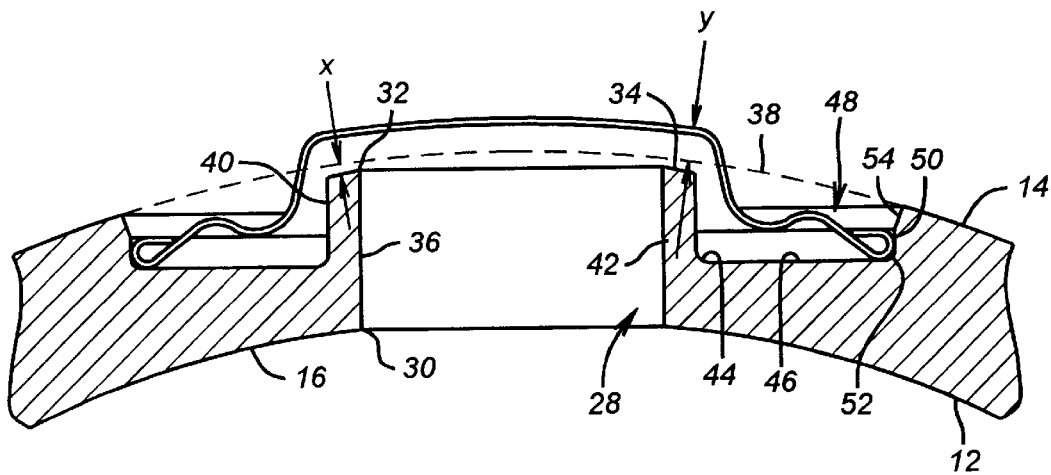
FIG. 3 is a sectional view of the acetabular shell of FIG. 1, in combination with the dome hole diaphragm of FIG. 2, taken along section line 3—3 of FIG. 1 and viewed in the direction of the arrows. The dome hole diaphragm is shown in a first position.
Figure 4:
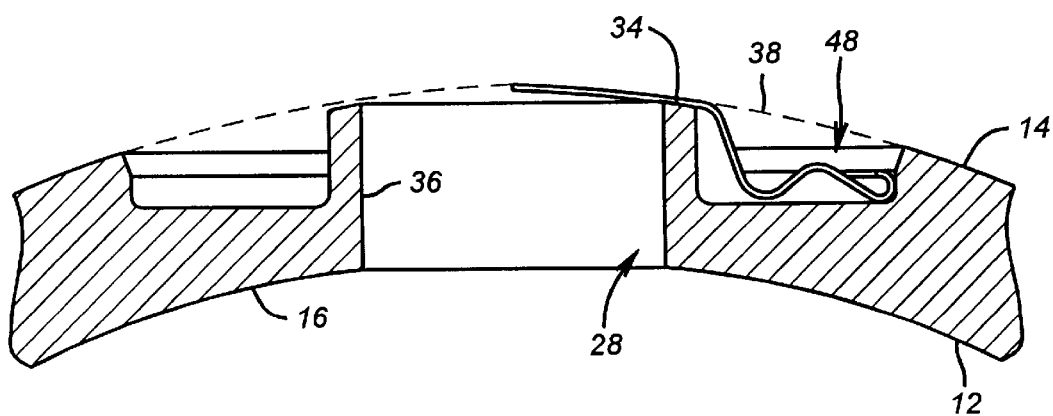
FIG. 4 is a sectional view of the acetabular shell of FIG. 1, in combination with the dome hole diaphragm of FIG. 2, taken along section line 3—3 of FIG. 1 and viewed in the direction of the arrows. The dome hole diaphragm is shown in a second position.

Referring again to FIG. 1, and also to FIGS. 3 and 4, acetabular shell 10 includes a dome hole 28 centered at the apex of dome region 18 in coaxial alignment with axis 26. Dome hole 28 has a distal open end 30 terminating at concave distal surface 16 and a proximal open end 32 terminating at a frusto-conical annular surface 34. Between concave distal surface 16 and frusto-conical annular surface 34, dome hole 28 is bounded by a substantially cylindrical side wall 36. If desired, side wall 36 can be internally threaded or otherwise configured to serve as an engagement interface for an instrument (not shown) for holding and positioning acetabular shell 10. Typically, such an instrument is used by the implanting physician to securely grasp the acetabular shell and place it in the reamed acetabulum. Such an instrument usually includes an elongate handle for controlling anteversion and adduction of the acetabular shell as it is implanted, and for transmitting axial driving forces to the shell. Frusto-conical annular surface 34 extends radially and distally from proximal open end 32 of dome hole 28, and is displaced distally a small distance "x" from an imaginary surface of curvature 38 extended from convex proximal surface 14 across dome region 18. The significance of the distal displacement "x" will be explained further below. Extending distally from the radially outward edge of frusto-conical annular surface 34 is a substantially cylindrical side wall 40 that, together with side wall 36, define therebetween an annular upstanding wall, or boss, 42. Side wall 40 terminates at a location proximal of distal concave surface 16, and transitions through a fillet 44 to join a bottom wall 46 of an annular groove 48 that surrounds upstanding boss 42. Annular groove 48, defined partially by side wall 40 and bottom wall 46, is further defined by an outer cylindrical side wall 50 that joins bottom wall 46 through a fillet 52, and that joins proximal convex surface 14 through a frusto-conical wall 54. Frusto-conical wall 54 extends proximally and radially outwardly from side wall 50 to form an annular bevel at the peripheral entrance to annular groove 48.

Figure 2:
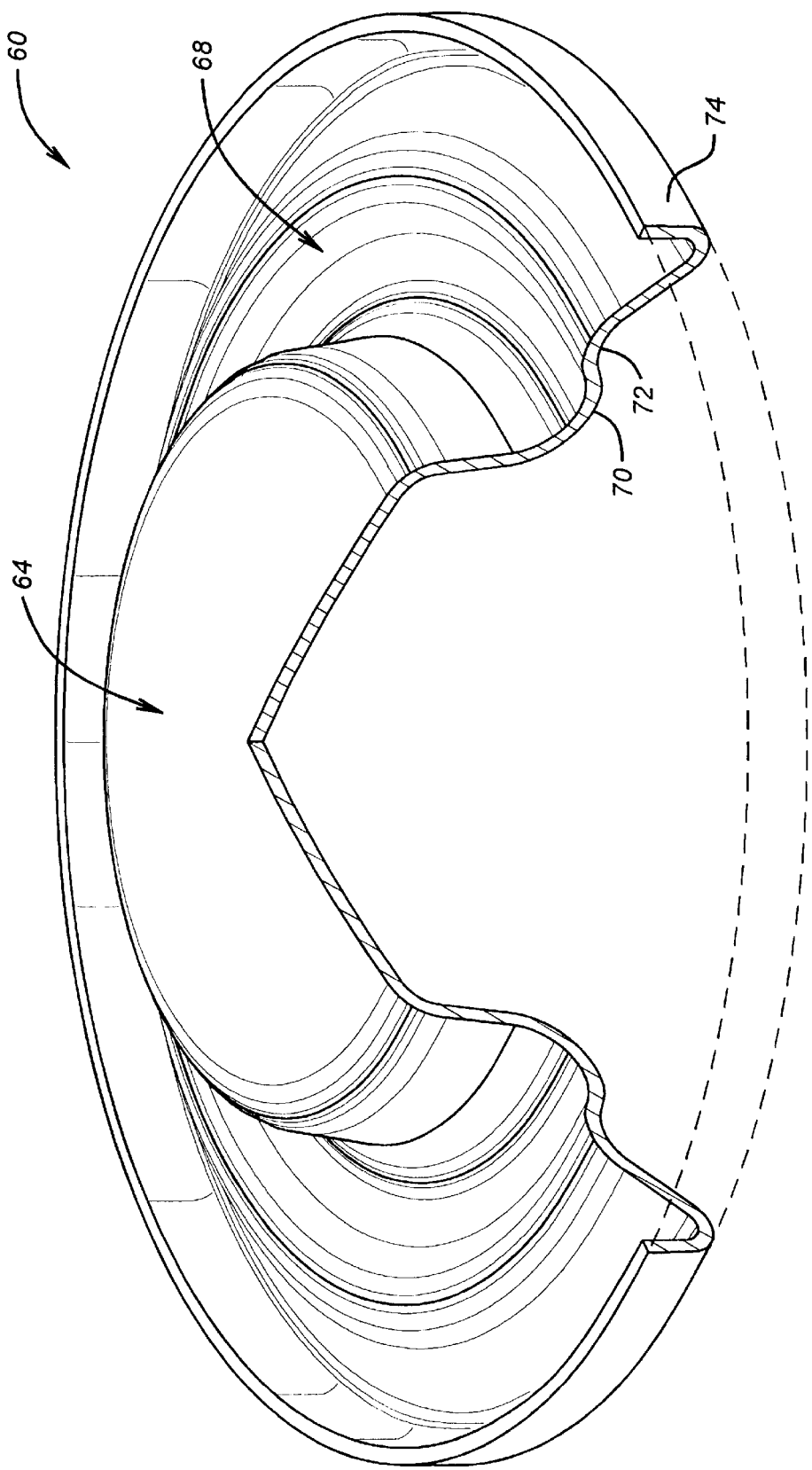
FIG. 2 is a perspective view, partially cut away, showing a dome hole diaphragm constructed in accordance with the present invention, for use with the acetabular shell of FIG. 1.

Referring to FIG. 2, a flexible diaphragm 60 is shown that is useful in combination with the acetabular shell 10 described above. More particularly, flexible diaphragm 60 is useful, when affixed to the dome region 18 of acetabular shell 10, for occluding dome hole 28. Occlusion of dome hole 28 is desirable to alleviate the risk of polyethylene debris migrating from shell cavity 22 through dome hole 28. Such polyethylene debris, according to a prevailing hypothesis, can be generated by frictional wear caused by micro-motion between the acetabular shell and its polyethylene bearing liner. By design, the polyethylene liner usually is intended to fit congruently against concave distal surface 16, without any articulation relative to the acetabular shell 10. Nevertheless, according to the hypothesis, some relative micro-motion inevitably occurs. The reason for concern over such polyethylene wear debris is that in vitro experiments have shown that fine polyethylene particles are osteolytic.

Figure 5:
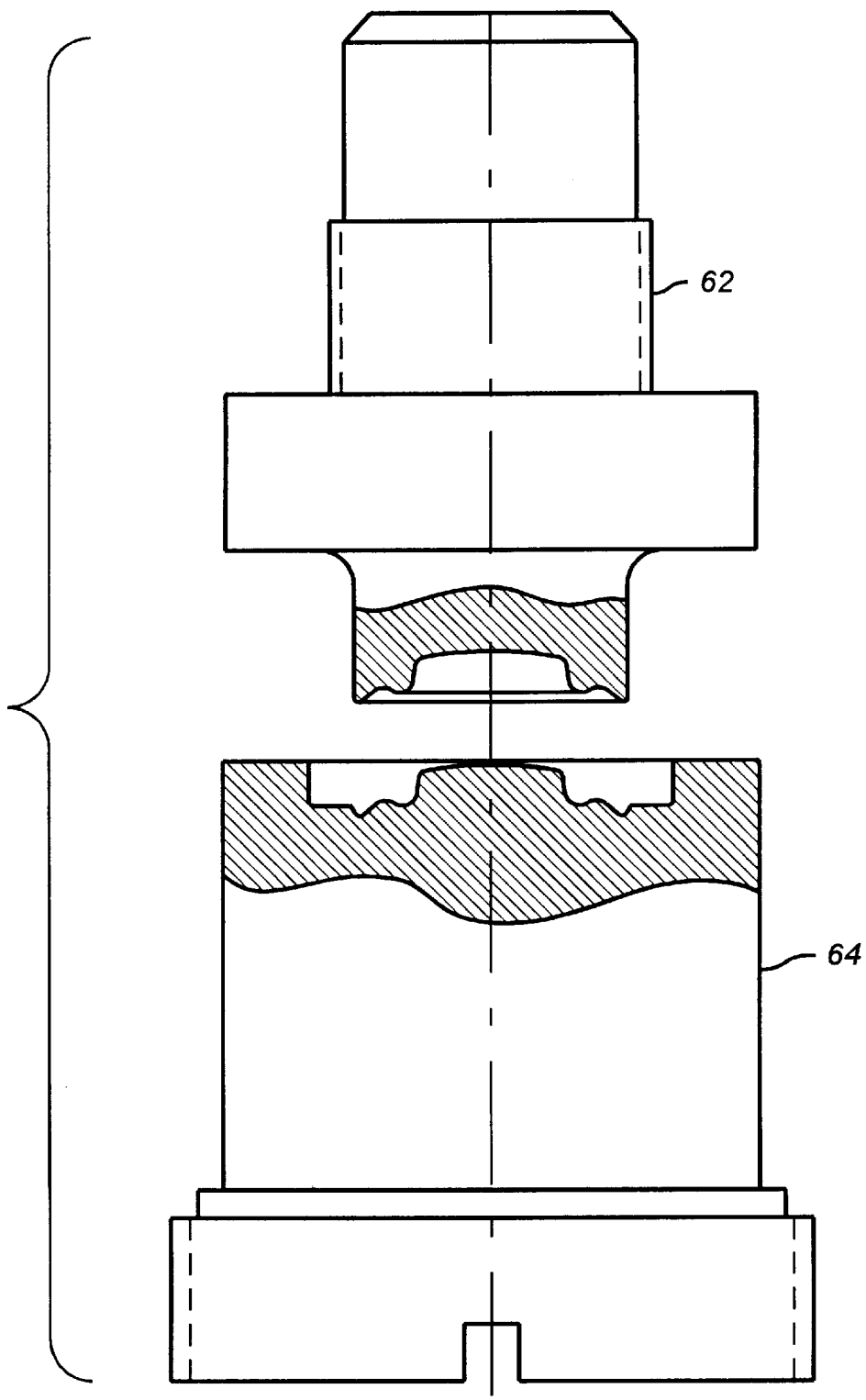
FIG. 5 is an elevation view of a punch and die tool useful for forming the dome hole diaphragm of FIG. 2.

Flexible diaphragm 60 is made of titanium or titanium alloy sheet metal and is formed by stamping the sheet metal between a mating punch 62 and die 64, as shown in FIG. 5. The sheet metal from which flexible diaphragm 60 is formed is preferred to have a thickness of about 0.005 inches, but may range from about 0.002 inches to about 0.010 inches in thickness. After stamping according to well-known machine tool operations, the resulting flexible diaphragm 60 includes a crown 64 that is generally spherical in curvature with a radius of curvature approximately equal to the radius of curvature of convex proximal surface 14 of acetabular shell 10. Crown 64 has a diametrical width somewhat greater than the diameter of side wall 40 of boss 42. Descending from crown 64 is an annular skirt 68 having annular undulations 70 and 72, which terminate in an annular rolled edge 74. Annular undulations 70 and 72 provide skirt 68 with sufficient flexibility and spring action to permit crown 64, when pressure is applied thereto, to be displaced distally relative to rolled edge 74, and yet spring back elastically upon release of the pressure.

Referring especially to FIGS. 3 and 4, the operation and advantages of flexible diaphragm 60 are made clear. In FIG. 3, flexible diaphragm 60 has been placed within annular groove 48 of acetabular shell 10 and is disposed in a first position. In FIG. 4, the flexible diaphragm 60 of FIG. 3 is shown disposed in a second position relative to acetabular shell 10. As manufactured, flexible diaphragm 60 has a natural, or unloaded, diameter slightly greater than the diameter of outer side wall 50 of annular groove 48. The preferred diametrical oversize is about 0.010 inch, which results in a press fit between rolled edge 74 and outer side wall 50. Diametrical compression of flexible diaphragm 60 and insertion into annular groove 48 is aided by the peripheral bevel provided by frusto-conical wall 54. When disposed in the first position, as shown in FIG. 3, crown 64 of flexible diaphragm 64 is displaced proximally of the imaginary surface of curvature 38 extended from convex proximal surface 14. The amount of displacement, "y", of crown 64 outside the curvature envelope 38 is about 1.0 mm to about 1.5 mm. When disposed in the second position, as shown in FIG. 4, the amount of displacement, "y", of crown 64 relative to the curvature envelope 38 is essentially zero. In other words, in the second position crown 64 does not extend proximally of the envelope of curvature 38. The amount of displacement, "x", by which frusto-conical annular surface 34 is disposed distally of the imaginary surface of curvature 38 is about the same as the wall thickness of crown 64 of flexible diaphragm 60. Hence, a load placed against the proximal surface of crown 64 causes annular skirt 68 to flex and crown 64 to be displaced distally until stopped by engagement with frusto-conical annular surface 34 of boss 42, as illustrated in FIG. 4.

One advantage of the present invention lies in the capability of flexible diaphragm 60 to be moved, against self-generated spring resistance, from the first position of FIG. 3 to the second position of FIG. 4, while simultaneously remaining secured within annular groove 48 and providing occlusion of dome hole 28. This capability allows the physician to verify, visually and tactily, that acetabular shell 10 has been fully seated against the reamed acetabular bone during implantation. If acetabular cup 10 has not been fully seated against bone, such that convex proximal surface 14 and its imaginary extension surface 38 are not immediately adjacent bone, then crown 64 will remain displaced from frusto-conical annular surface 34 of boss 42, leaving a gap therebetween that can be seen, or felt using a suitable probing tool, through dome hole 28 from the distal open end thereof. Whereas, if acetabular cup 10 is fully seated against the reamed acetabular bone, then crown 64, through engagement with bone, will have been displaced into the second position of FIG. 4, in which no gap exists between crown 64 and frusto-conical surface 34 of boss 42. Visual or tactile confirmation that the gap is closed verifies that the acetabular shell is fully seated.

Another advantage of the present invention lies in the characteristic that the dome hole remains occluded at all times without interfering with use of the dome hole as an engagement interface for a positioning tool. This is because the occluding element, flexible diaphragm 60, never intrudes within dome hole 28, thereby leaving all of the cylindrical surface 36 available as a tool-engaging surface.

Although the flexible diaphragm 60 of the preferred embodiment can be used with only a press-fit engagement within annular groove 48, it is preferred to provide a more secure connection between flexible diaphragm 60 and acetabular shell 10 by making a sintered metallurgical bond. After the flexible diaphragm 60 is pressed in place within annular groove 48, the combination of shell and diaphragm is heated in an oven in an inert atmosphere approaching the temperature at which the diaphragm and shell become "plastic". This temperature is held for a period of time sufficient to allow the metal parts to become bonded to each other at the press-fit interfaces.

The present invention has been illustrated and described with particularity in terms of a preferred embodiment. Nevertheless, it should be understood that no limitation of the scope of the invention is intended thereby. The scope of the invention is defined by the claims appended hereto. It should also be understood that variations of the particular embodiment described herein, incorporating the principles of the present invention, will occur to those of ordinary skill in the art and yet be within the scope of the appended claims.

I claim:

1. An acetabular component for an implantable hip joint prosthesis comprising:

a generally cup-shaped acetabular shell having an outer convex proximal surface and a concave distal surface defining a shell wall therebetween, said shell wall having an apex and an annular rim, said shell wall defining a dome hole therethrough at said apex, said dome hole having an open proximal end and an open distal end;

a flexible diaphragm affixed to said outer convex surface of said shell wall and occluding said open proximal end of said dome hole, said flexible diaphragm being flexibly moveable between a first position and a second position;

said flexible diaphragm in said first position being spaced from said open proximal end of said dome hole; and said flexible diaphragm in said second position being in engagement with said open proximal end of said dome hole.

2. The acetabular component of claim 1, in which said flexible diaphragm is spring biased toward said first position.

3. The acetabular component of claim 2, in which said flexible diaphragm in said first position extends proximally beyond an imaginary surface of curvature coextensive with said convex proximal surface of said acetabular shell.

4. The acetabular component of claim 3, in which said flexible diaphragm in said second position does not extend proximally beyond an imaginary surface of curvature coextensive with said convex proximal surface of said acetabular shell.

5. The acetabular component of claim 4, in which said open proximal end of said dome hole is spaced distally from an imaginary surface of curvature coextensive with said convex proximal surface of said acetabular shell.

6. The acetabular component of claim 5, in which said flexible diaphragm includes a crown, an annular edge, and a flexible annular skirt between said crown and said annular edge.

7. The acetabular component of claim 6, in which said annular edge is affixed to said shell wall by a sintered metallurgical bond.

8. The acetabular component of claim 7, in which said flexible annular skirt includes an annular undulation.

9. The acetabular component of claim 3, in which said shell wall includes a proximal annular surface that circumscribes said open proximal end of said dome hole.

10. The acetabular component of claim 9, in which said flexible diaphragm includes a crown overlying said proximal annular surface of said shell wall.

11. The acetabular component of claim 10, in which said proximal annular surface of said shell wall is spaced distally from an imaginary surface of curvature coextensive with said convex proximal surface of said acetabular shell.

12. The acetabular component of claim 11, in which said crown of said flexible diaphragm has a wall thickness, and the proximal annular surface of said shell wall is spaced distally from said imaginary surface of curvature by a distance about equal to the wall thickness of said crown.

13. The acetabular component of claim 12, in which said flexible diaphragm in said second position does not extend proximally beyond an imaginary surface of curvature coextensive with said convex proximal surface of said acetabular shell.

14. The acetabular component of claim 13, in which said flexible diaphragm includes an annular edge, and a flexible annular skirt between said crown and said annular edge.

15. The acetabular component of claim 14, in which said flexible annular skirt includes an annular undulation.

16. The acetabular component of claim 15, in which said shell wall includes an annular recess in said convex proximal surface that circumscribes said proximal annular surface and is disposed distally therefrom to define an upstanding boss around said dome hole that terminates proximally at said proximal annular surface.

17. The acetabular component of claim 16, in which said annular edge is affixed to said shell wall by a sintered metallurgical bond.

18. An acetabular component for an implantable hip joint prosthesis comprising:

a generally cup-shaped acetabular shell having a proximal surface and a distal surface defining a shell wall therebetween, said shell wall having an apex, a dome hole through said apex, and an annular groove in said proximal surface around said dome hole;

a diaphragm having a disc-shape with a crown portion at its center and a circular edge along its outer circumference, wherein said circular edge is positioned in said annular groove and said crown portion is positioned above said dome hole; and said diaphragm being flexibly moveable between a first position and a second position, wherein said crown portion is spaced apart from said proximal surface of said shell wall while in said first position and said crown portion is against said proximal surface of said shell wall while in said second position.

19. The acetabular component of claim 18 in which:

an annular wall extends between said annular groove and said dome hole;

said annular wall includes a top annular surface that forms part of said proximal surface of said shell wall;

said crown portion is displaced from said top annular surface in said first position; and said crown portion is positioned against said top annular surface in said second position.

20. The acetabular component of claim 19 in which said crown portion moves about 1.0 mm to 1.5 mm from said first position to said second position.

21. The acetabular component of claim 18 in which said diaphragm further includes an annular skirt extending between said crown portion and said edge.

22. The acetabular component of claim 21 in which said skirt includes at least one undulation that provides a spring bias and enables movement between said first and second positions.

23. The acetabular component of claim 21 in which said skirt includes at least one elastic undulation that provides a bias between said crown portion and said edge.

24. The acetabular component of claim 23 in which said undulation flexes between an unbiased state while said diaphragm is in said first position and a biased state while said diaphragm is in said second position.

25. The acetabular component of claim 18 in which said diaphragm further includes a flexible skirt extending between said crown portion and said edge, wherein said skirt has a spring resistance that flexes between an unbiased state while said diaphragm is in said first position and a biased state while said diaphragm is in said second position.

26. The acetabular component of claim 18 in which:

said diaphragm includes a crown; and said diaphragm moves from said first position to said second position when a force is applied to said crown.

27. The acetabular component of claim 26 in which said diaphragm moves from said second position back to said first position when said force is removed from said crown.

* * * * *